United States Patent [19]

Källstrand et al.

[11] Patent Number: 5,533,505
[45] Date of Patent: Jul. 9, 1996

[54] DISPOSABLE INHALER

[75] Inventors: Göran Källstrand, Bjärred; Per-Gunnar Nilsson, Malmö, both of Sweden

[73] Assignee: Astra Aktiebolag, Sodertalje, Sweden

[21] Appl. No.: 295,709

[22] PCT Filed: Mar. 3, 1993

[86] PCT No.: PCT/EP93/00473

§ 371 Date: Sep. 2, 1994

§ 102(e) Date: Sep. 2, 1994

[87] PCT Pub. No.: WO93/17728

PCT Pub. Date: Sep. 16, 1993

[30] Foreign Application Priority Data

Mar. 4, 1992 [EP] European Pat. Off. .............. 92850046

[51] Int. Cl.⁶ ................ A61M 15/00; A61M 16/00; B05D 7/14; B65D 83/06
[52] U.S. Cl. ................ 128/203.15; 128/203.21
[58] Field of Search ................ 128/203.15, 203.21, 128/203.12, 203.19, 203.23; 206/528; 604/58; 222/636

[56] References Cited

U.S. PATENT DOCUMENTS

| 4,817,80 | 4/1989 | Williams et al. | 206/484 |
|---|---|---|---|
| 2,549,303 | 4/1949 | Friden | 128/206 |
| 4,265,236 | 5/1981 | Pacella | 128/203.23 |
| 4,811,731 | 3/1989 | Newell et al. | 128/203.15 |
| 4,841,964 | 6/1989 | Hurka et al. | 128/203.15 |
| 5,035,237 | 7/1991 | Newell et al. | 128/203.15 |
| 5,042,472 | 8/1991 | Bunin | 128/203.15 |
| 5,239,991 | 8/1993 | Chawla et al. | 128/203.15 |

FOREIGN PATENT DOCUMENTS

| 0404454 | 12/1990 | European Pat. Off. | 128/203.05 |
|---|---|---|---|
| WO89/01348 | 2/1989 | WIPO | |
| WO92/04069 | 3/1992 | WIPO | |

OTHER PUBLICATIONS

International Search Report (European Patent Office).

*Primary Examiner*—Kimberly L. Asher
*Attorney, Agent, or Firm*—Fish & Richardson

[57] ABSTRACT

The invention relates to a disposable breath-actuated inhaler comprising a tubular housing forming an air flow path being open at both ends, one end forming an air inlet (4) and one end forming an air outlet (5), the housing comprising a compartment (3) for storing a pharmaceutical powder to be inhaled. The compartment (3) for storing the pharmaceutical powder is located close to the air inlet (4) and is covered by a thin foil (6) sealing the compartment in an airtight way which can be removed from the compartment from outside the housing, the housing being shaped with a constriction (9) adjacent the powder compartment (3) such that a turbulent air stream will be obtained at the constriction upon inhalation which will lift the powder out from the compartment (3) and mix the powder into the air stream.

19 Claims, 3 Drawing Sheets

DISPOSABLE INHALER

TECHNICAL FIELD OF THE INVENTION

The present invention relates to a breath-actuated disposable inhaler of the kind having a generally tubular shape and having two ends, one end forming an air inlet and one end forming an air outlet, the inhaler containing a pharmaceutical powder comprising particles of a respirable size which are to be inhaled.

BACKGROUND OF THE INVENTION

Disposable, breath-actuated inhalers of the kind described above are for instance disclosed in WO 89/01348, U.S. Pat. No. 4,265,236 and EP-A-0404454.

EP-A-0404454 discloses a disposable, breath-actuated inhaler comprising a chamber for a pharmaceutical powder, said chamber being provided with an air inlet and with an air outlet. The air inlet and outlet are covered by a common cover. The powder is disposed loosely in the comparatively large chamber which means that the powder will not necessarily be located at that location at which the air flow is most efficient.

U.S. Pat. No. 4,265,236 discloses a tubular disposable, breath-actuated inhaler comprising a flexible tube, the ends of which normally are sealingly inserted into each other. This kind of seal will not necessarily be moisture-proof. There furthermore is a risk that some amount of the powder may fall out of the inhaler when the ends of the tube are pulled apart. WO 89/01348, in the embodiment most of interest here, discloses a tubular, disposable inhaler which is Sealed in both ends by means of twist-off caps. The. pharmaceutical powder is loosely disposed in the inhaler and, as in the other inhalers described above, there is a risk that some powder is lost when the inhaler is opened.

The objects of the invention are to provide a disposable inhaler of the kind described above in which the dose of pharmaceutical powder can be determined accurately and in which the pharmaceutical powder can be stored hermetically sealed and moisture-proof. The dose delivered by different specimens of the same inhaler should generally be constant. The inhaler finally should be easy to prepare for use and easy to use as well as being easy and cheap to manufacture.

BRIEF DESCRIPTION OF THE APPENDED DRAWINGS

FIG. 1 shows a perspective view of an inhaler according to the invention,

FIG. 2 shows a perspective view of an inhaler according to FIG. 1 but showing the two main parts of the inhaler in an unassembled state, FIGS. 3A–3C show different stages in the opening of the powder compartment of the inhaler of FIG. 1, FIG. 4 shows an end view of the air inlet of the inhaler in FIG. 1, FIGS. 5–7 show different possible embodiments of the constriction adjacent the powder compartment.

DETAILED DESCRIPTION OF A PREFERRED EMBODIMENT OF THE INVENTION

Figure 1:
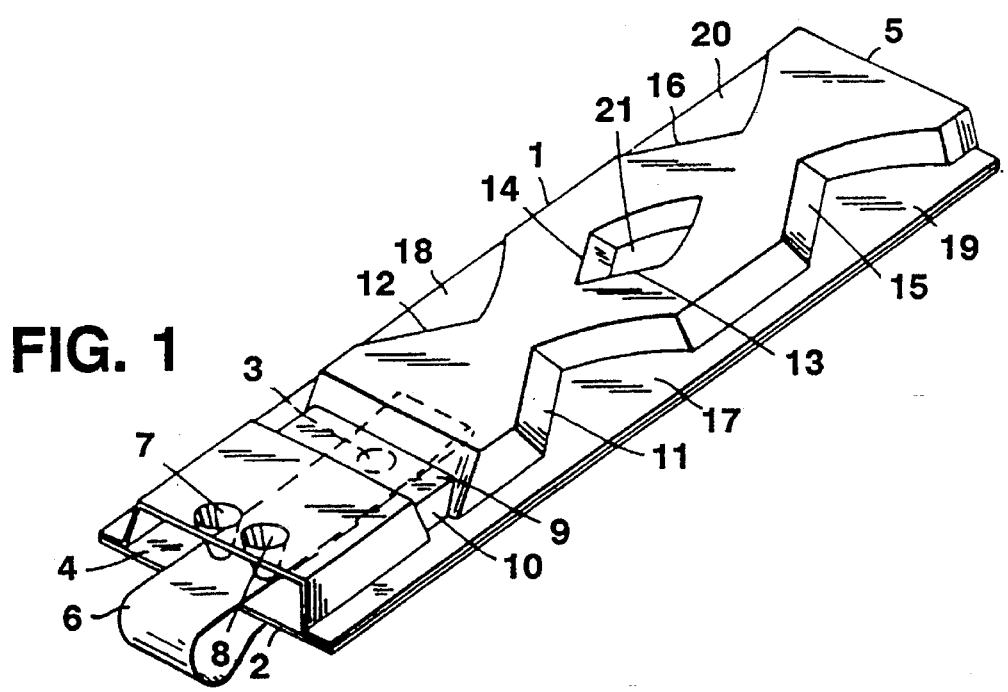

A preferred embodiment of the invention is disclosed in FIGS. 1–4. In FIG. 1 the inhaler can be seen in a fully assembled condition and ready for use. As can be seen, the inhaler essentially comprises two elongate main parts, an upper part 1 which is made of a moulded sheet of plastic material and a lower part 2 preferably made of aluminum foil laminated with plastic. The upper part I is U-shaped with a substantially rectangular shape. The width of the upper part is several times the height. The lower part is generally flatland the two parts thus form a tubular housing defining an air conduit or air flow path with an air inlet 4 and an air outlet 5. A part-spherical depression or recess 3 indicated with a dashed line is located close to the air inlet 4. The recess 3 forms a powder compartment and is covered by a tape 6 which preferably is made of aluminum foil, also laminated with plastic. The recess 3 may also be provided with one or several small through-holes 24 in the bottom. The hole or holes 24 should be large enough to allow the entry of air into the recess from the underside of the lower part, but sufficiently small to prevent any part of the powder from falling out through the hole(s).

As indicated, the end of the part of the tape 6 covering the recess 3 is located between the recess 3 and the air inlet 4. The tape is attached to the lower part 2 around the powder compartment by means of a relatively weak weld 22 which can be seen in FIG. 2. The end of the tape is attached by a comparatively large and thus stronger weld in front of the compartment, as seen in the intended direction of the airflow. The free part of the tape 6 is bent backwards over the recess 3 and extends out through the air inlet 4. In this particular embodiment, the free part of the tape is guided and held by two conical projections 7,8 extending downwards from the upper part 1. The free part of the tape may be bent in a loop to the underside of the lower part 2 and attached to the lower part all around the recess 3 by a relatively weak weld, thus sealing the hole 24 and the=recess 3. The tape should be sufficiently long to extend past the recess 3, thus forming a tab 25 to serve as a grip for tearing the tape away.

A constriction in the flow path in the form of a ridge 9 oriented perpendicularly relative to the direction of the flow path is located above the powder compartment. The ridge is formed as a depression 9 in the upper part 1. The ridge is delimited at each end by an abutment 10.

The inhaler is further provided with deaggregation means after the powder compartment, as seen in the direction of the intended air flow through the inhaler. These deaggregation means comprise a number of oblique planar surfaces which are oriented at an angle of about 30° relative to the longitudinal direction of the inhaler, it surprisingly having been found that the most efficient angle of a planar surface relative to the air flow direction for disintegrating powder agglomerations is about 30°. Since the air flow will be deflected to some extent by the planar surface, the flow direction will not coincide fully with the longitudinal direction, but the above angle has been chosen as being the best compromise. The angle can however be varied between 20° and 50° with a preferred range of 25°–35°.

The planar surfaces are oriented generally perpendicularly relative to the lower part 2, or at least as perpendicularly as the method of manufacturing the inhaler allows. The planar surfaces are located in such a way that their projections onto a cross-sectional plane substantially cover the entire cross-section of the inhaler. The projections preferably should overlap to some extent in order to ensure that any larger particles or agglomerations entrained in the air flow will impact on at least one such surface. In the preferred embodiment the planar surfaces 11, 12, 13, 14, 15, 16 are located on the upstream ends of two pairs of indentions 17, 18; 19, 20, formed into the sides of the upper part 1 and on the upstream end of a central depression 21 located between said indentations forming an island in the flow path. The downstream ends of said indentations and said depression taper in the direction of the air flow and have a smooth, rounded shape in order to obtain good aerodynamic conditions without any areas where the powder entrained in the air flow could settle.

Figure 2:
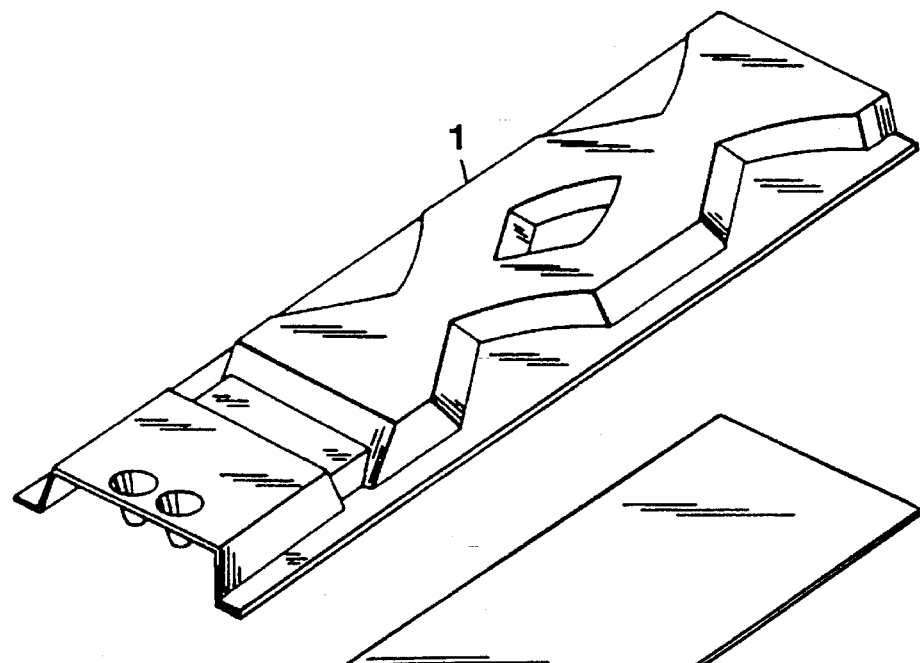
Figure 2:
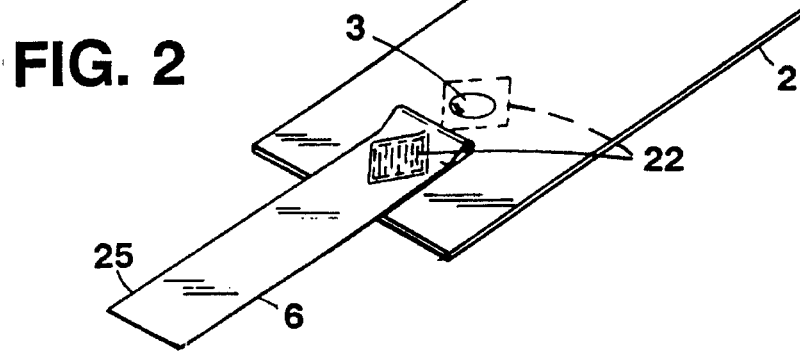
Figure 3A:
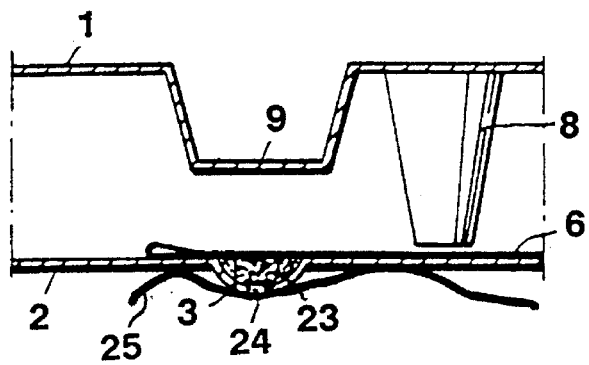
Figure 3B:
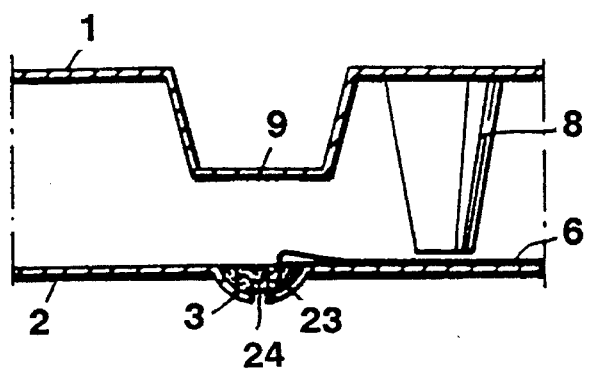
Figure 3C:
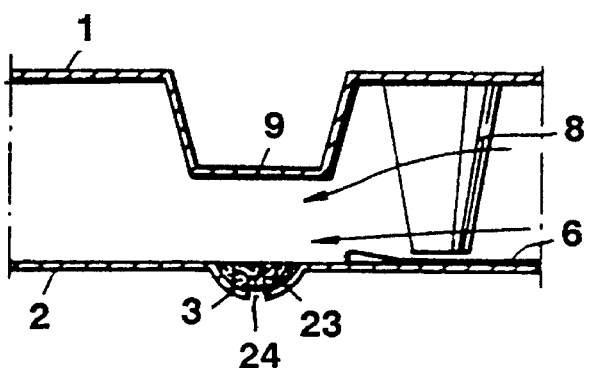
Figure 4:
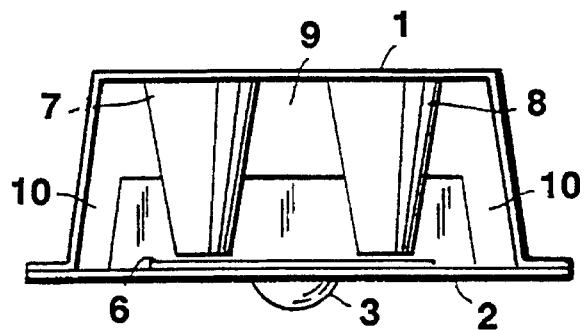
Figure 5:
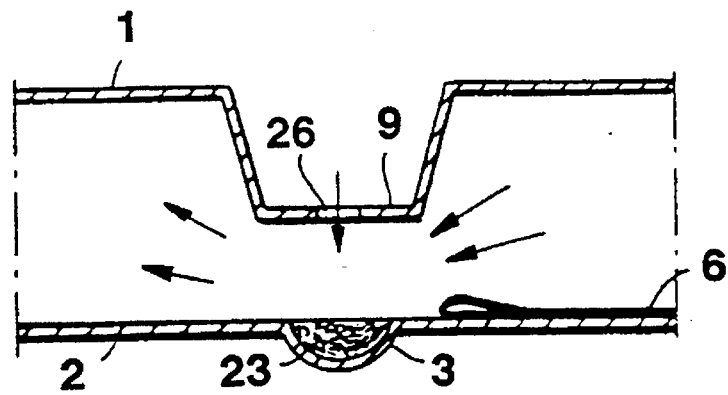

The two main parts of the inhaler are shown separated in FIG. 2. Apart from the details Shown in FIG. 1, the powder compartment 3 is shown opened, the tape 6 having been pulled outwardly through the air inlet. The shape of the (broken) weld 22 can be seen on the tape 6 and around the powder compartment 3. As can be seen, the shape of the weld has been chosen to be the perimeter of a square oriented with one diagonal parallel-with the longitudinal extent of the inhaler. This means that the disengagement of the tape from the lower part 2 will be facilitated since the tearing action will both start and end at a corner. Since the weld holding the inner end of the tape is .broad and strong, the user will feel when the compartment has been uncovered by means of the increased resistance.

FIGS. 3A–3C show different stages in the opening of the powder compartment 3 by pulling the tape 6, thus exposing the powder 23. FIG. 3A shows the tape 6 attached around the recess 3 on the under side of the lower part, thus covering the hole 24 whilst leaving a tearing tab 25.

The end view in shown in FIG. 4 more clearly illustrates the inter-relationship between the upper part 1, the lower part 2, the powder compartment 3, the tape 6, the conical projections 7, 8, the ridge 9 and the abutments 10.

When the inhaler is to be used, the inhaler is held more or less horizontal with the flat half 2 facing downwards. The free end of the tape 6 is pulled by means of the tab 25, thus exposing the hole 23 and the powder in the powder compartment 3. The two conical projections 7, 8 will hold the tape 6 flat against the lower part 2 and thus prevent the tape from occluding the constriction in front of the powder compartment. The user then inserts the air outlet into the mouth and inhales through the inhaler. The resultant air flow through the inhaler will become very turbulent in the region of the constriction and the pharmaceutical powder will be lifted out of the powder compartment and mixed with the air flow. Any particles adhering to the tape may also be entrained with the air flow since the part of the tape originally covering the powder compartment also will lie directly in the flow path. By admitting air into the bottom of the recess 3, the through-hole 24 will counteract any sub-pressures in the bottom of the recess which might impede the lifting of the powder out of the recess.

Tests have shown that the dose leaving a typical powder compartment (e.g. about 0.5 mg) located at a constriction having an area of about 10–12 $mm^2$ will remain essentially constant at air flow rates varying from 30 l/min to 60 l/min.

The powder-laden air will then flow from the constriction to the deaggregation means. The angle of attack of the oblique surfaces will entail that the lighter particles, i.e. the particles within the respirable range, <6 μm, will be deflected from the surface without sticking thereto and thus mainly will follow the air flow, whereas the heaver particles and agglomerates will impact on and rebound from the planar surfaces and in this way be broken up into smaller particles. As mentioned above, an angle of about 30° may be optimal.

In this case tests again have shown that the percentage of particles within the respirable range in the dose to be inhaled will remain substantially constant at air flow rates ranging from 30 l/min to 60 l/min.

That the dose of respirable particles remains substantially constant over a wide range of air flows is important in order to minimize the difference between patients with different inhalation capacities.

It should be noted that the tubular shape of the inhaler makes it possible to mount a rubber ball or similar over the air inlet. By the means thereof the powder could be ejected from the inhaler into the throat of the patient in synchronization with the breathing of the patient by a helper if the patient should be incapable to use the inhaler by himself.

As mentioned above, the lower part 2 of the inhaler as well as the tape 6 preferably are made of aluminum foil laminated or coated with a suitable plastic. The aluminum will ensure the desired protection against moisture whereas the plastic will ensure that the tape can be welded to the lower part and that the lower part can be welded to the upper part. The lower part may for instance consist of a aluminum foil having a thickness of 45 μ which on one side is covered with a layer of oriented polyamide which is 25 μ thick and on the other side is covered by a layer of polypropene which is 60 μ thick. The upper part is preferably made of polypropene being 300 or 400 μ thick. The upper part can be transparent so that the user can see if the dose has been ejected from the powder compartment.

The tape may be made of a laminate having a "peel"-effect comprising polyester, aluminum and a layer comprising a polymer mixture of polybuten and polypropene.

The choice of material in the inhaler should be adapted to the drug to be used. The above materials have been chosen with a specific drug (budesonide) in mind, these materials releasing a dose of this drug more easily.

The composition of the pharmaceutical powder of course is quite optional and the powder may for instance comprise a pure active substance, a mixture of different active substances or a mixture of active substance(s) with adjuvant(s). It should be pointed out that the scope of choice of drugs is widened considerably due to the moisture-proof containment of the drug in the powder compartment.

The inhaler may be manufactured in the following way. A series of hemispherical indentations are formed in a strip of laminated aluminum foil in order to shape powder compartments. If the indentations are to be provided with through-holes, these are also formed at this stage. The indentations are filled with drugs and are topped off by means of scrapers, which will ensure a substantially uniform size of the different doses. An aluminum tape laminated with plastic is then welded over each indentation and around the indentation on the outside of the lower part.

The lower parts are then welded to upper parts and the strip is cut to form individual inhalers which are ready for packaging and use. The upper parts are moulded from sheets of plastic. In the moulding procedure care should be taken to ensure that the side walls of the upper part are as perpendicular as possible relative to the upper side in order to ensure an air flow which is as uniform as possible throughout the entire cross-section of the inhaler. The function of the abutments 10 primarily are to prevent distortion of the ridge forming the constriction during the welding process.

Possible modifications of the invention

The invention of course can be modified in many ways within the scope of the appended claims.

Thus the ridge 9 forming the constriction can be designed in different ways in order to enhance the lifting action of the air flow on the powder. Some examples thereof can be found in FIGS. 5–7.

FIG. 5 illustrates how the ridge 9 can be provided with a small hole 26 centrally above the powder compartment 3.

When the patient inhales through the inhaler, additional air will be directed more or less perpendicularly down into the powder compartment, thus enhancing the turbulent action in the vicinity of the powder compartment.

Figure 6:
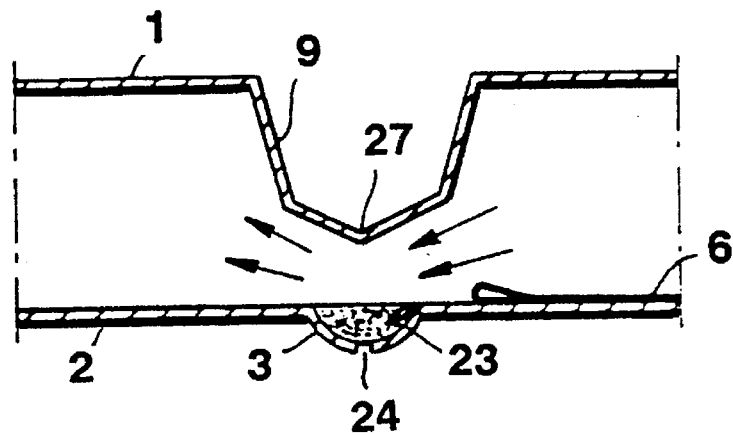
Figure 7:
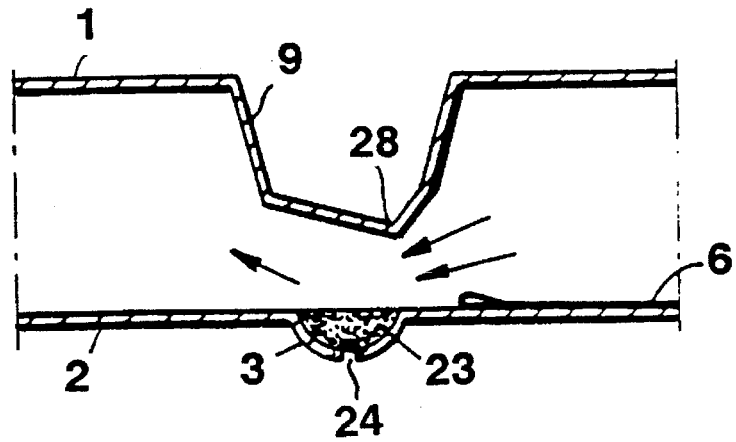

FIGS. 6 and 7 illustrate two alternative embodiments wherein the ridge has been provided with an edge 27 or 28 oriented along the longitudinal extent of the ridge which will direct air flow more directly into the powder compartment.

These embodiments will however require a higher degree of precision in the manufacturing in order to obtain the desired effect than the embodiment described above and will therefore be more difficult to manufacture.

The ridge 9 forming the constriction has been illustrated as being generally trapezoid in cross-section and as being generally rectilinear in longitudinal section. It should however be pointed out that the constriction may be shaped in many different ways within the scope of the appended claims.

The powder compartment can of course have another shape than a half-spherical shape and may for instance be elliptical, the minor axis thereof being parallel with the direction of the air flow, or may be otherwise trough-shaped. It is of course also possible to have several indentations, for instance if it is desired to increase the dose in an exactly defined way. As mentioned above, the powder compartment can be designed without the hole(s) 24. Two separate tapes furthermore can be used to seal the recess 3 respectively the hole(s) 24.

The projections 7,8 can be shaped otherwise than conically and may for instance be shaped such that they direct a greater part of the air flow more directly past the powder compartment. They also could be integrated with the abutments 10.

The tape 6 could also be arranged in such a manner that it can be removed entirely from the lower part 2. In this case the projections 7,8 are not needed, at least not for the purpose of guiding and holding the tape.

The deaggregation means can be designed in other ways than in the form of planar surfaces oriented at an angle of about 20°–50° relative to the direction of the air flow. This angle can of course also be varied outside this range and the surfaces do not necessarily have to be planar.

The material in the lower part and the tape does not necessarily have to comprise aluminum and may be any plastic material having the necessary impermeability and stiffness or having been treated to have these properties.

It is also conceivable to make the inhaler from a single sheet which is rolled or folded after having been moulded in an appropriate way.

We claim:

1. A disposable breath-actuated inhaler for delivering a dose of a finely divided powder to a patient comprising a housing defining a chamber, said chamber having an air inlet, an air outlet in fluid communication with the air inlet, and an air flow path extending between said inlet and said outlet a compartment, containing a dose of finely divided powder, located in a region of said chamber intermediate said inlet and said outlet, said compartment defining a volume to hold the dose and having an opening which exposes a surface of said dose to said air flow path, said compartment including a through-hole positioned beneath the finely divided powder, said through hole selectively opened to ambient air to allow ambient air to enter the compartment, a removable cover disposed sealingly over said opening in said compartment and confining the dose of finely divided powder within the compartment prior to delivery, and a constriction means in said air flow path adjacent the powder compartment positioned to induce sufficient turbulence in an air stream produced upon removal of said removable cover and subsequent inhalation to lift the powder out from the compartment and mix the powder into the air stream for delivery through the air outlet.

2. An inhaler according to claim 1 wherein said powder compartment includes a plurality of through-holes.

3. An inhaler according to claim 1, wherein said housing comprises an upper half and a substantially flat lower half having an indentation forming the powder compartment, said two halves being sealingly joined along their longitudinal sides.

4. An inhaler according to claim 3, wherein the upper part is moulded from a thin plastic sheet.

5. An inhaler according to claim 3 or 4, wherein said constriction means is formed as a depression in said upper part which depression is oriented transversely relative to the longitudinal extent of the tubular housing and located above the powder compartment.

6. An inhaler according to claim 3, wherein the lower half comprises a laminate including an aluminum foil layer and a plastic layer.

7. An inhaler according to claim 1, wherein the cover comprises a thin foil in the shape of a tape having a free end extending out through the air inlet, said tape being attached around the edges of the powder compartment by relatively weak welds.

8. An inhaler according to claim 7, wherein an inner end of the tape, spaced from said free end, is attached to an inner surface of the lower half between the air inlet and the powder compartment, and the tape extends away from the air inlet past the powder compartment, and then bends backwards so as to extend toward and out through the air inlet.

9. An inhaler according to claim 8, wherein the weak welds form a point facing downstream in the airflow path in order to facilitate the initiation of the tearing action along the welds when the tape is pulled out of the housing to expose the powder.

10. An inhaler according to claim 8 wherein said free end of said tape is attached to an outer surface of said lower part and positioned to seal said through-hole.

11. An inhaler according to claim 1 wherein said housing further comprises a projection extending downwardly from the upper half between the powder compartment and the air inlet for holding the tape against the lower half of the housing in order to prevent the tape from obstructing the air flow path.

12. An inhaler according to claim 1 wherein said housing further comprises deaggregation means located in the air flow path between the powder compartment and the air outlet.

13. An inhaler according to claim 11, wherein said deaggregation means comprise a plurality of planar surfaces defining said air flow path, each surface being oriented at an angle of from about 20°–50° relative to the longitudinal direction of the tubular housing, said surfaces being disposed generally perpendicularly to a plane through the longitudinal axis of the tubular housing, a projection of the planar surfaces onto a cross-section of the housing substantially covering said cross-section.

14. An inhaler according to claim 13 wherein said angle is from about 25°–35°.

15. An inhaler according to claim 1 wherein said compartment includes two through-holes.

16. An inhaler according to claim 15 wherein said through-holes are positioned at a deepest portion of said compartment.

17. An inhaler according to claim 1 wherein said removable cover is removable from outside the housing.

18. An inhaler according to claim 17 wherein said cover comprises a thin foil.

19. An inhaler according to claim 17 or 18 wherein said housing comprises an upper half and a substantially flat lower half having an indentation defining the powder compartment, said two halves being sealingly joined along their longitudinal edges.

* * * * *